United States Patent
Board et al.

(10) Patent No.: US 9,655,719 B2
(45) Date of Patent: May 23, 2017

(54) SURGICAL HEART VALVE FLEXIBLE STENT FRAME STIFFENER

(71) Applicant: St. Jude Medical, Cardiology Division, Inc., St. Paul, MN (US)

(72) Inventors: Stephanie Marie Board, West St. Paul, MN (US); Jeffrey Ross Ambrus, West St. Paul, MN (US); Joseph Donald Smith, Vadnais Heights, MN (US); Deborah Ann Wojcik, Maplewood, MN (US); Mai Sia Vue, Brooklyn Park, MN (US); Aaron J. Chalekian, Savage, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 173 days.

(21) Appl. No.: 13/752,915

(22) Filed: Jan. 29, 2013

(65) Prior Publication Data
US 2014/0214158 A1 Jul. 31, 2014

(51) Int. Cl.
A61F 2/24 (2006.01)

(52) U.S. Cl.
CPC ............. *A61F 2/24* (2013.01); *A61F 2/2409* (2013.01); *A61F 2/2418* (2013.01); *A61F 2220/0075* (2013.01); *A61F 2250/0018* (2013.01)

(58) Field of Classification Search
CPC .............................. A61F 2/2409; A61F 2/2418
USPC ........... 623/2.1, 2.12, 2.13, 2.14, 2.15, 2.16, 623/2.17, 2.18, 2.19, 2.38
See application file for complete search history.

(56) References Cited

U.S. PATENT DOCUMENTS

| | | |
|---|---|---|
| 3,657,744 A | 4/1972 | Ersek |
| 3,755,823 A | 9/1973 | Hancock |
| 4,275,469 A | 6/1981 | Gabbay |
| 4,491,986 A | 1/1985 | Gabbay |
| 4,725,274 A * | 2/1988 | Lane ..................... A61F 2/2412 623/2.18 |
| 4,759,758 A | 7/1988 | Gabbay |
| 4,878,906 A | 11/1989 | Lindemann et al. |
| 4,922,905 A | 5/1990 | Strecker |
| 4,994,077 A | 2/1991 | Dobben |

(Continued)

FOREIGN PATENT DOCUMENTS

| | | |
|---|---|---|
| DE | 19857887 A1 | 7/2000 |
| DE | 10121210 A1 | 11/2002 |

(Continued)

OTHER PUBLICATIONS

International Search Report and Written Opinion for Application No. PCT/US2014/012238 dated Apr. 28, 2014.

(Continued)

*Primary Examiner* — David Isabella
*Assistant Examiner* — Suba Ganesan
(74) *Attorney, Agent, or Firm* — Lerner, David, Littenberg, Krumholz & Mentlik, LLP

(57) ABSTRACT

A prosthetic heart valve includes an annular frame having annularly spaced commissure portions and an annulus portion disposed near an inflow edge, a fabric covering at least a portion of the frame and a valve assembly connected to the frame at the commissure portions, the valve assembly including a plurality of leaflets. A stiffening member is disposed about the frame to limit ovalization of the frame when a radial force is applied to the frame.

21 Claims, 13 Drawing Sheets

(56) References Cited

U.S. PATENT DOCUMENTS

| | | |
|---|---|---|
| 5,035,709 A | 7/1991 | Wieting et al. |
| 5,411,552 A | 5/1995 | Andersen et al. |
| 5,480,423 A | 1/1996 | Ravenscroft et al. |
| 5,843,167 A | 12/1998 | Dwyer et al. |
| 5,855,601 A | 1/1999 | Bessler et al. |
| 5,935,163 A | 8/1999 | Gabbay |
| 5,961,549 A | 10/1999 | Nguyen et al. |
| 6,077,297 A | 6/2000 | Robinson et al. |
| 6,083,257 A | 7/2000 | Taylor et al. |
| 6,090,140 A | 7/2000 | Gabbay |
| 6,102,944 A * | 8/2000 | Huynh et al. ............... 623/2.15 |
| 6,214,036 B1 | 4/2001 | Letendre et al. |
| 6,264,691 B1 | 7/2001 | Gabbay |
| 6,267,783 B1 | 7/2001 | Letendre et al. |
| 6,368,348 B1 | 4/2002 | Gabbay |
| 6,419,695 B1 | 7/2002 | Gabbay |
| 6,468,660 B2 | 10/2002 | Ogle et al. |
| 6,488,702 B1 | 12/2002 | Besselink |
| 6,517,576 B2 | 2/2003 | Gabbay |
| 6,533,810 B2 | 3/2003 | Hankh et al. |
| 6,582,464 B2 | 6/2003 | Gabbay |
| 6,610,088 B1 | 8/2003 | Gabbay |
| 6,623,518 B2 | 9/2003 | Thompson et al. |
| 6,685,625 B2 | 2/2004 | Gabbay |
| 6,719,789 B2 | 4/2004 | Cox |
| 6,730,118 B2 | 5/2004 | Spenser et al. |
| 6,783,556 B1 | 8/2004 | Gabbay |
| 6,790,230 B2 | 9/2004 | Beyersdorf et al. |
| 6,814,746 B2 | 11/2004 | Thompson et al. |
| 6,830,584 B1 | 12/2004 | Seguin |
| 6,869,444 B2 | 3/2005 | Gabbay |
| 6,893,460 B2 | 5/2005 | Spenser et al. |
| 6,908,481 B2 | 6/2005 | Cribier |
| 7,018,406 B2 | 3/2006 | Seguin et al. |
| 7,025,780 B2 | 4/2006 | Gabbay |
| 7,137,184 B2 | 11/2006 | Schreck |
| 7,160,322 B2 | 1/2007 | Gabbay |
| 7,247,167 B2 | 7/2007 | Gabbay |
| 7,267,686 B2 | 9/2007 | DiMatteo et al. |
| 7,311,730 B2 | 12/2007 | Gabbay |
| 7,374,573 B2 | 5/2008 | Gabbay |
| 7,381,218 B2 | 6/2008 | Schreck |
| 7,452,371 B2 | 11/2008 | Pavcnik et al. |
| 7,510,572 B2 | 3/2009 | Gabbay |
| 7,524,331 B2 | 4/2009 | Birdsall |
| RE40,816 E | 6/2009 | Taylor et al. |
| 7,585,321 B2 | 9/2009 | Cribier |
| 7,682,390 B2 | 3/2010 | Seguin |
| 7,731,742 B2 | 6/2010 | Schlick et al. |
| 7,803,185 B2 | 9/2010 | Gabbay |
| 7,846,203 B2 | 12/2010 | Cribier |
| 7,846,204 B2 | 12/2010 | Letac et al. |
| 7,871,435 B2 * | 1/2011 | Carpentier et al. ........... 623/2.15 |
| 7,914,569 B2 | 3/2011 | Nguyen et al. |
| D648,854 S | 11/2011 | Braido |
| D652,926 S | 1/2012 | Braido |
| D652,927 S | 1/2012 | Braido et al. |
| D653,341 S | 1/2012 | Braido et al. |
| D653,342 S | 1/2012 | Braido et al. |
| D653,343 S | 1/2012 | Ness et al. |
| D654,169 S | 2/2012 | Braido |
| D654,170 S | 2/2012 | Braido et al. |
| D660,432 S | 5/2012 | Braido |
| D660,433 S | 5/2012 | Braido et al. |
| D660,967 S | 5/2012 | Braido et al. |
| D684,692 S | 6/2013 | Braido |
| 2002/0036220 A1 | 3/2002 | Gabbay |
| 2003/0023303 A1 | 1/2003 | Palmaz et al. |
| 2003/0050694 A1 | 3/2003 | Yang et al. |
| 2003/0130726 A1 | 7/2003 | Thorpe et al. |
| 2004/0049262 A1 | 3/2004 | Obermiller et al. |
| 2004/0093075 A1 | 5/2004 | Kuehne |
| 2004/0176839 A1 | 9/2004 | Huynh et al. |
| 2004/0210304 A1 | 10/2004 | Seguin et al. |
| 2005/0096726 A1 | 5/2005 | Sequin et al. |
| 2005/0137695 A1 | 6/2005 | Salahieh et al. |
| 2005/0137697 A1 | 6/2005 | Salahieh et al. |
| 2005/0203605 A1 | 9/2005 | Dolan |
| 2005/0240263 A1 * | 10/2005 | Fogarty et al. ............... 623/2.38 |
| 2005/0256566 A1 | 11/2005 | Gabbay |
| 2006/0008497 A1 | 1/2006 | Gabbay |
| 2006/0074484 A1 | 4/2006 | Huber |
| 2006/0122692 A1 | 6/2006 | Gilad et al. |
| 2006/0149360 A1 | 7/2006 | Schwammenthal et al. |
| 2006/0173532 A1 | 8/2006 | Flagle et al. |
| 2006/0178740 A1 | 8/2006 | Stacchino et al. |
| 2006/0206202 A1 | 9/2006 | Bonhoeffer et al. |
| 2006/0229718 A1 * | 10/2006 | Marquez ...................... 623/2.38 |
| 2006/0241744 A1 | 10/2006 | Beith |
| 2006/0241745 A1 | 10/2006 | Solem |
| 2006/0259120 A1 | 11/2006 | Vongphakdy et al. |
| 2006/0259137 A1 | 11/2006 | Artof et al. |
| 2006/0265056 A1 | 11/2006 | Nguyen et al. |
| 2006/0276813 A1 | 12/2006 | Greenberg |
| 2007/0010876 A1 | 1/2007 | Salahieh et al. |
| 2007/0027534 A1 | 2/2007 | Bergheim et al. |
| 2007/0043435 A1 | 2/2007 | Seguin et al. |
| 2007/0055358 A1 | 3/2007 | Krolik et al. |
| 2007/0067029 A1 | 3/2007 | Gabbay |
| 2007/0093890 A1 | 4/2007 | Eliasen et al. |
| 2007/0100435 A1 | 5/2007 | Case et al. |
| 2007/0118210 A1 | 5/2007 | Pinchuk |
| 2007/0213813 A1 | 9/2007 | Von Segesser et al. |
| 2007/0233228 A1 | 10/2007 | Eberhardt et al. |
| 2007/0244545 A1 | 10/2007 | Birdsall et al. |
| 2007/0244552 A1 | 10/2007 | Salahieh et al. |
| 2007/0288087 A1 | 12/2007 | Fearnot et al. |
| 2008/0021552 A1 | 1/2008 | Gabbay |
| 2008/0039934 A1 | 2/2008 | Styrc |
| 2008/0071369 A1 | 3/2008 | Tuval et al. |
| 2008/0082164 A1 | 4/2008 | Friedman |
| 2008/0097595 A1 | 4/2008 | Gabbay |
| 2008/0114452 A1 | 5/2008 | Gabbay |
| 2008/0125853 A1 | 5/2008 | Bailey et al. |
| 2008/0140189 A1 | 6/2008 | Nguyen et al. |
| 2008/0147183 A1 | 6/2008 | Styrc |
| 2008/0154355 A1 | 6/2008 | Benichou et al. |
| 2008/0154356 A1 | 6/2008 | Obermiller et al. |
| 2008/0243245 A1 | 10/2008 | Thambar et al. |
| 2008/0255662 A1 | 10/2008 | Stacchino et al. |
| 2008/0262602 A1 | 10/2008 | Wilk et al. |
| 2008/0269879 A1 | 10/2008 | Sathe et al. |
| 2008/0294248 A1 * | 11/2008 | Yang .................... A61F 2/2418 623/2.17 |
| 2009/0112309 A1 | 4/2009 | Jaramillo et al. |
| 2009/0138079 A1 | 5/2009 | Tuval et al. |
| 2010/0004740 A1 | 1/2010 | Seguin et al. |
| 2010/0036484 A1 | 2/2010 | Hariton et al. |
| 2010/0049306 A1 | 2/2010 | House et al. |
| 2010/0087907 A1 | 4/2010 | Lattouf |
| 2010/0131055 A1 | 5/2010 | Case et al. |
| 2010/0168778 A1 | 7/2010 | Braido |
| 2010/0168839 A1 | 7/2010 | Braido et al. |
| 2010/0185277 A1 | 7/2010 | Braido et al. |
| 2010/0191326 A1 | 7/2010 | Alkhatib |
| 2010/0204781 A1 | 8/2010 | Alkhatib |
| 2010/0204785 A1 | 8/2010 | Alkhatib |
| 2010/0217382 A1 | 8/2010 | Chau et al. |
| 2010/0249911 A1 | 9/2010 | Alkhatib |
| 2010/0249923 A1 | 9/2010 | Alkhatib et al. |
| 2010/0286768 A1 | 11/2010 | Alkhatib |
| 2010/0298931 A1 | 11/2010 | Quadri et al. |
| 2011/0029072 A1 | 2/2011 | Gabbay |
| 2011/0264207 A1 * | 10/2011 | Bonhoeffer ........... A61F 2/2412 623/2.18 |
| 2012/0065729 A1 | 3/2012 | Pintor et al. |
| 2012/0078357 A1 | 3/2012 | Conklin |

FOREIGN PATENT DOCUMENTS

| | | |
|---|---|---|
| DE | 202008009610 U1 | 12/2008 |
| EP | 0850607 A1 | 7/1998 |
| EP | 1000590 A1 | 5/2000 |
| EP | 1360942 A1 | 11/2003 |

(56) References Cited

FOREIGN PATENT DOCUMENTS

| | | | |
|---|---|---|---|
| EP | 1584306 | A1 | 10/2005 |
| EP | 1598031 | A2 | 11/2005 |
| FR | 2847800 | A1 | 6/2004 |
| FR | 2850008 | A1 | 7/2004 |
| WO | 9117720 | A1 | 11/1991 |
| WO | 9716133 | A1 | 5/1997 |
| WO | 9832412 | A2 | 7/1998 |
| WO | 9913801 | A1 | 3/1999 |
| WO | 0128459 | A1 | 4/2001 |
| WO | 0149213 | A2 | 7/2001 |
| WO | 0154625 | A1 | 8/2001 |
| WO | 0156500 | A2 | 8/2001 |
| WO | 0176510 | A2 | 10/2001 |
| WO | 0236048 | A1 | 5/2002 |
| WO | 0247575 | A2 | 6/2002 |
| WO | 03047468 | A1 | 6/2003 |
| WO | 2006073626 | A2 | 7/2006 |
| WO | 2007071436 | A2 | 6/2007 |
| WO | 2008070797 | A2 | 6/2008 |
| WO | 2010008548 | A2 | 1/2010 |
| WO | 2010096176 | A1 | 8/2010 |
| WO | 2010098857 | A1 | 9/2010 |

OTHER PUBLICATIONS

Catheter-implanted prosthetic heart valves, Knudsen, L.L., et al., The International Journal of Artificial Organs, vol. 16, No. 5 1993, pp. 253-262.

Design U.S. Appl. No. 29/375,243, filed Sep. 20, 2010.

Is It Reasonable to Treat All Calcified Stenotic Aortic Valves With a Valved Stent?, 579-584, Zegdi, Rachid, MD, PhD et al., J. of the American College of Cardiology, vol. 51, No. 5, Feb. 5, 2008.

Percutaneous aortic valve replacement: resection before implantation, 836-840, Quaden, Rene et al., European J. of Cardio-thoracic Surgery, 27 (2005).

Ruiz, Carlos, Overview of PRE-CE Mark Transcatheter Aortic Valve Technologies, Euro PCR (powerpoint)—dated May 25, 2010?.

Transluminal Aortic Valve Placement, Moazami, Nader, et al., ASAIO Journal, 1996; 42:M381-M385.

Transluminal Catheter Implanted Prosthetic Heart Valves, Andersen, Henning Rud, International Journal of Angiology 7:102-106 (1998).

Transluminal implantation of artificial heart valves, Andersen, H. R., et al., European Heart Journal (1992) 13, 704-708.

* cited by examiner

700

SURGICAL HEART VALVE FLEXIBLE STENT FRAME STIFFENER

BACKGROUND OF THE INVENTION

This invention relates to prosthetic heart valves, and more particularly to surgically-implanted prosthetic heart valves.

There is increasing interest in prosthetic heart valves that use tissue material for the leaflets of the valve. Such valves tend to be less thrombogenic than mechanical prosthetic heart valves. This can reduce or eliminate the need for a patient who has received such a prosthesis to take anti-coagulant medication on a long-term basis. Tissue-based heart valves may also have other advantages, such as quieter operation. Because of the interest in such valves, improvements to them are greatly desired. Improved methods of making such valves are also sought.

Despite the various improvements that have been made to prosthetic heart valves, conventional devices, systems, and methods suffer from some shortcomings. For example, in certain procedures, prosthetic heart valves may be implanted in a native valve annulus without first resecting the native valve leaflets. The valves may have critical clinical issues because of the nature of the stenotic leaflets that are left in place. Additionally, it may be difficult or impossible to treat patients with uneven calcification, aortic valve bi-cuspid disease, and/or valve insufficiency with the current designs.

The reliance on evenly calcified leaflets could lead to several problems such as: (1) perivalvular leakage (PV leak), (2) valve migration, (3) mitral valve impingement, (4) conduction system disruption, (5) coronary blockage, etc., all of which can have severely adverse clinical outcomes. To reduce these adverse events, the optimal valve would seal and anchor adequately within the native valve annulus without the need for excessive radial force, protrusion into the left ventricular outflow tract (LVOT), etc., that could harm nearby anatomy and physiology.

There therefore is a need for further improvements to these prosthetic heart valves, as well as to the systems and methods for implanting these prosthetic heart valves. Among other advantages, the present invention may address one or more of these needs.

SUMMARY OF THE INVENTION

In some embodiments, a prosthetic heart valve includes an annular frame having annularly spaced commissure portions and an annulus portion disposed near an inflow edge, a fabric covering a portion of the frame, a valve assembly connected to the frame at the commissure portions, the valve assembly including a plurality of leaflets and a stiffening member closely arranged adjacent an annulus portion of the frame to limit ovalization of the frame when a radial force is applied to the frame.

In some examples, the stiffening member may include a ring disposed about a portion of the frame. The ring may include at least one chamfer. The stiffening member may include a metal. The stiffening member may be disposed about the annulus portion of the frame. The stiffening member may be biocompatible. The stiffening member may be disposed about the outer diameter of the frame.

In some examples, the stiffening member may be disposed adjacent the inner diameter of the frame. The stiffening member may be at least partially wrapped in a fabric. The stiffening member may include a scalloped portion. The stiffening member may include at least one chamfer. A chamfer may be formed on a bottom edge the stiffening member.

BRIEF DESCRIPTION OF THE DRAWINGS

Various embodiments of the presently disclosed valves are described herein with reference to the drawings, wherein.

Various embodiments of the present invention will now be described with reference to the appended drawings. It is to be appreciated that these drawings depict only some embodiments of the invention and are therefore not to be considered limiting of its scope.

DETAILED DESCRIPTION

Figure 1:
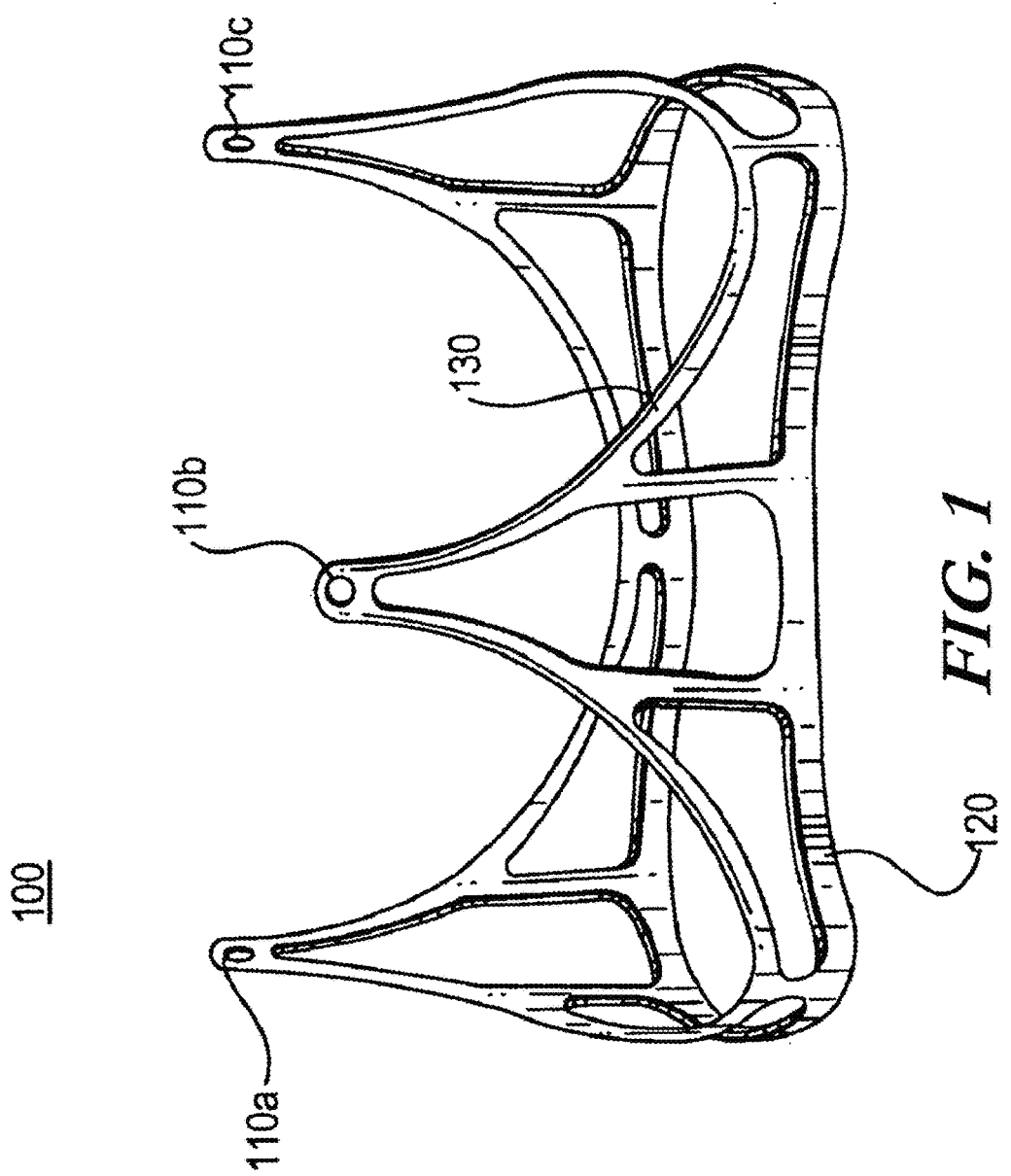
FIG. 1 is a perspective view of an example of a frame of a prosthetic heart valve.

An illustrative embodiment of a frame 100 of an artificial heart valve in accordance with the invention is shown in FIG. 1. Frame 100 has a generally hollow, annular shape. Frame 100 is referred to as "hollow" because the interior that is bounded by its annular structure is open. Frame 100 is typically made of a biologically compatible metal, such as titanium (e.g., Ti 6Al-4V ELI Grade 5). A typical technique for making frame 100 is to cut it from a tube using a laser. Frame 100 is then typically electro-polished.

Because the valve of the illustrative embodiment being discussed is a tricuspid valve (e.g., for use in replacing a patient's aortic valve), frame 100 has three commissure portions or regions 110a, 110b, and 110c that are equally spaced from one another around the circumference of the frame. Each commissure portion stands up from the annularly continuous base portion of the frame. The base portion includes a lower-most, blood-inflow edge portion 120. This blood-inflow edge portion is scalloped as one proceeds around the frame to approximately match the natural scallop of the native valve annulus. In particular, this scallop rises in the vicinity of each commissure region, and falls between each annularly adjacent pair of commissures.

Frame 100 also includes an annularly continuous blood-outflow edge portion 130 (which merges with and becomes part of each commissure region 110). Outflow edge portion 130 is much more deeply scalloped than inflow edge portion 120. In particular, outflow edge portion 130 rises adjacent each commissure 110 (actually merging into each commissure as noted above), and falls between each annularly adjacent pair of commissures.

The inflow edge 120, outflow edge 130, and flexibility of frame 100 are designed to help ensure proper opening and coaptation of the valve leaflets of the prosthetic heart valve during use. (Coaptation is the coming together of the free edges of the valve leaflets when the valve is closed.) Frame 100 is further designed to decrease maximum stresses in the frame during use, which gives the finished valve an increased safety factor.

Although titanium is mentioned above as a typical material from which frame 100 may be formed, other biologically compatible materials may also be used. Some examples of other materials that may be suitable for use in making frame 100 include ELGILOY® MP35N or polymers such as PEEK or acetal.

Figure 2:
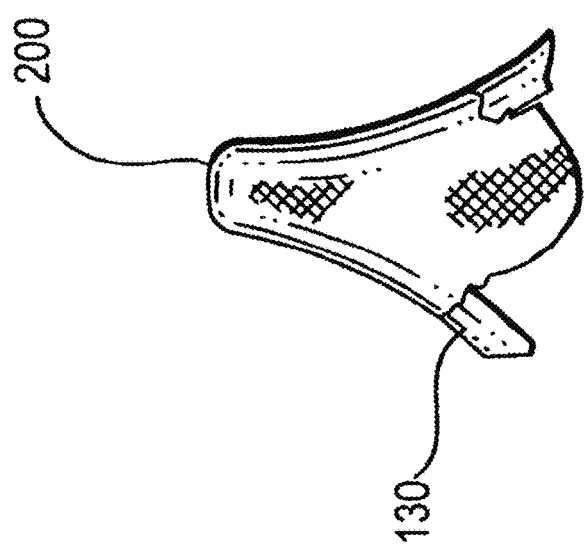
FIG. 2 is a perspective view of a representative portion of a commissure tip.

FIG. 2 illustrates a subsequent possible step in the manufacture of the illustrative embodiment being described. This is the addition of a sleeve-like fabric covering 200 over the top of each commissure post. Fabric commissure tip covers 200 help reduce the possibility that the frame commissure tips may poke through subsequently added components. An illustrative fabric that is suitable for use in making coverings 200 is reemay fabric, which is a spun form of polyester. Each tip cover 200 may be secured to the associated commissure tip with sutures.

Figure 3:
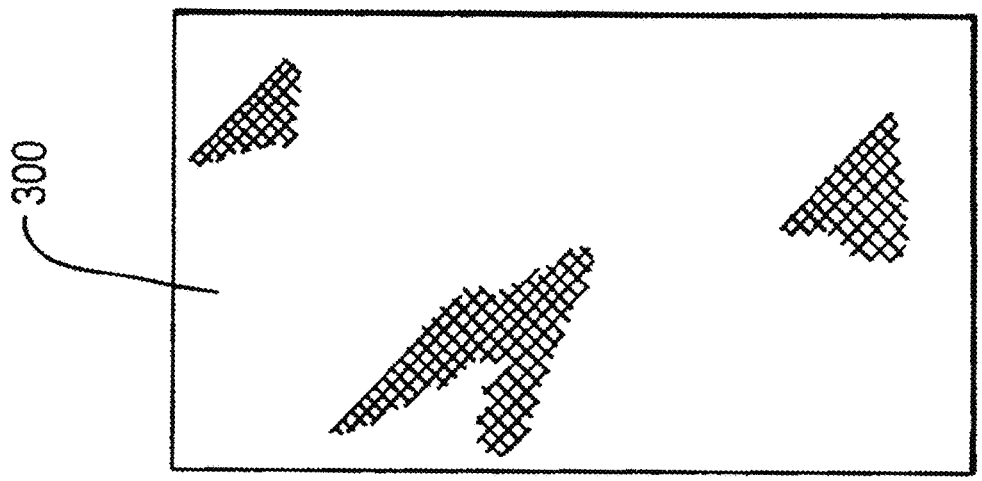
FIG. 3 is an elevational view of a fabric prior to assembly to the frame.
Figure 4:
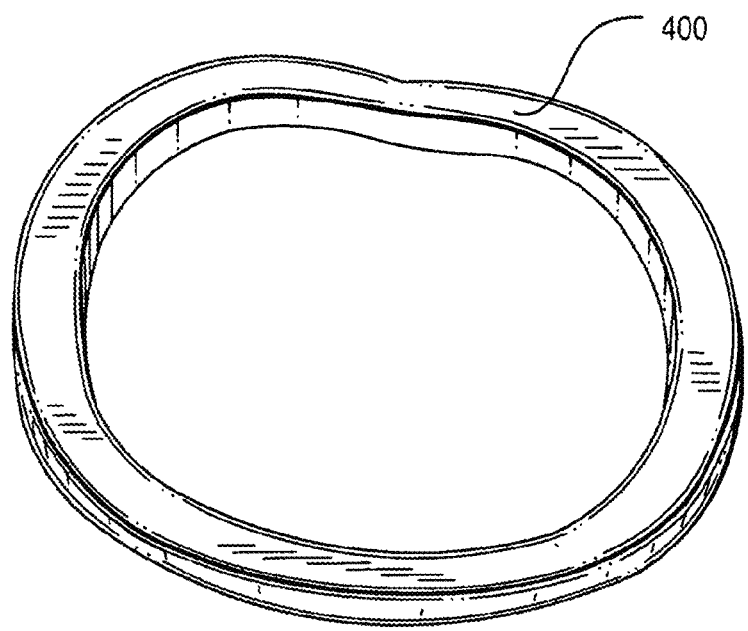
FIG. 4 is a perspective view of a silicone ring prior to assembly to the frame.
Figure 5:
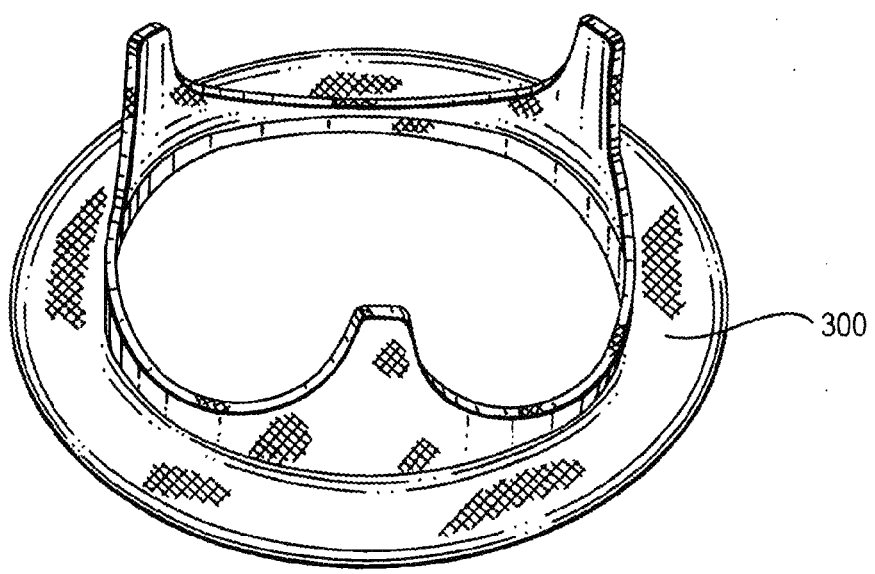
FIG. 5 is a perspective view of an assembly of the components from FIGS. 1-4.

FIGS. 3-5 illustrate further possible components and steps in the manufacture of the illustrative embodiment being described. FIG. 3 shows an illustrative embodiment of a polyester fabric tube 300; FIG. 4 shows an illustrative embodiment of a silicone cuff filler ring 400; and FIG. 5 shows an assembly 500 that includes frame 100 (with post tip coverings 200) and silicone cuff filler ring 400 covered inside and out by fabric tube 300. For example, frame 100 (with coverings 200) and ring 400 may be placed coaxially around the outside of a lower portion of fabric tube 300. Ring 400 may be located outside inflow edge portion 120. The upper portion of sleeve 300 may then be pulled down over the outside of components 100 and 400 and pulled tightly enough to conform to outflow edge portion 130 as shown in FIG. 5. Sutures may be used to hold the above-described components together in the condition shown in FIG. 5. In particular, all of components 100, 200, and 400 are completely covered inside and out by fabric 300. Ring 400 is located adjacent inflow edge portion 120 and follows the scalloping of the inflow edge portion all the way around assembly 500. The upper portion of fabric 300 conforms closely to frame 100 above ring 400, and in particular, the upper portion of the fabric follows the scalloped outflow edge portion 130 all the way around assembly 500. Fabric tube 300 may be capable of slight stretching to assume the shape of outflow edge portion 130.

Figure 6:
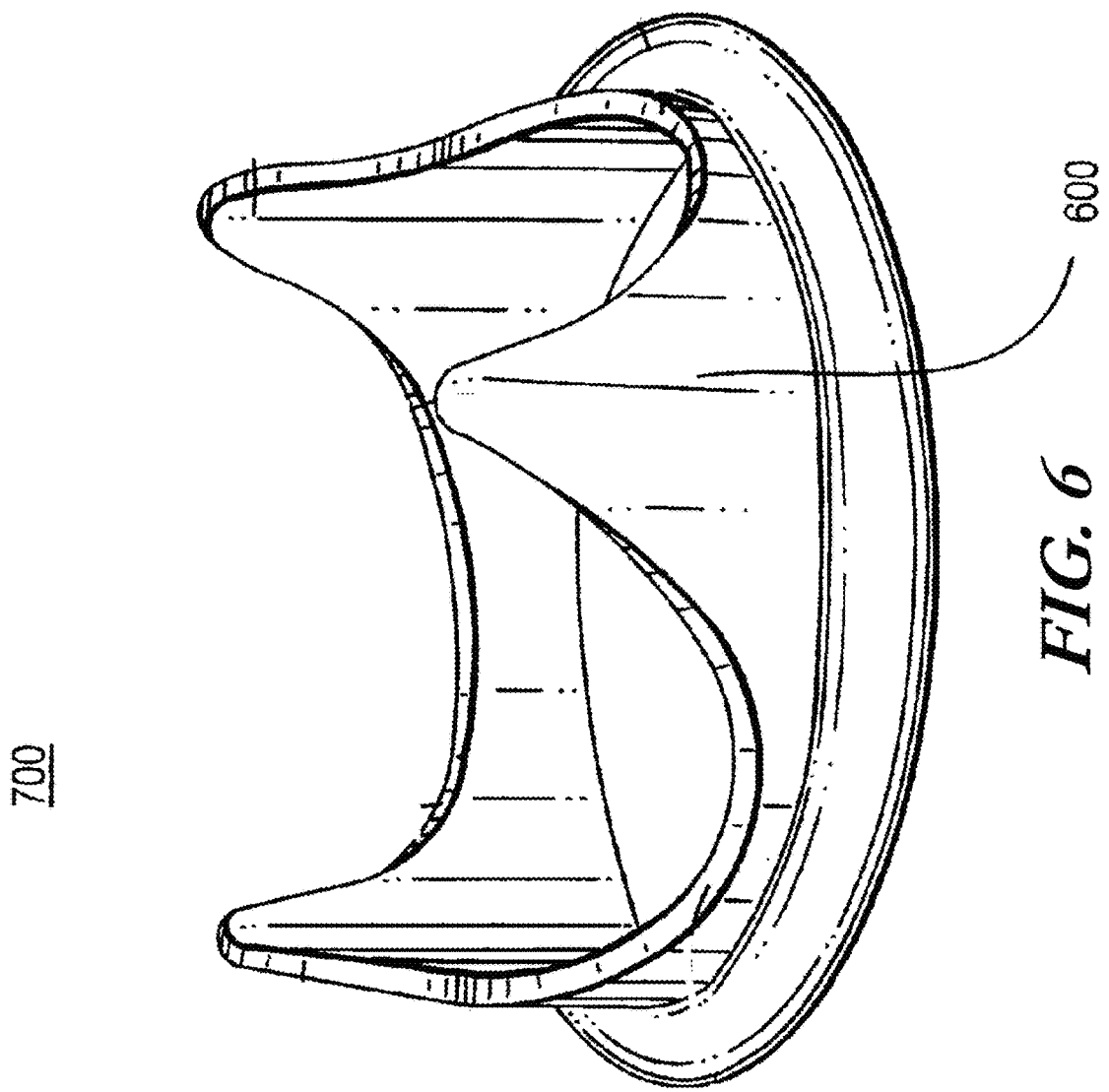
FIGS. 6 and 7 are, respectively, perspective top and bottom views of the assembly of FIG. 5.
Figure 7:
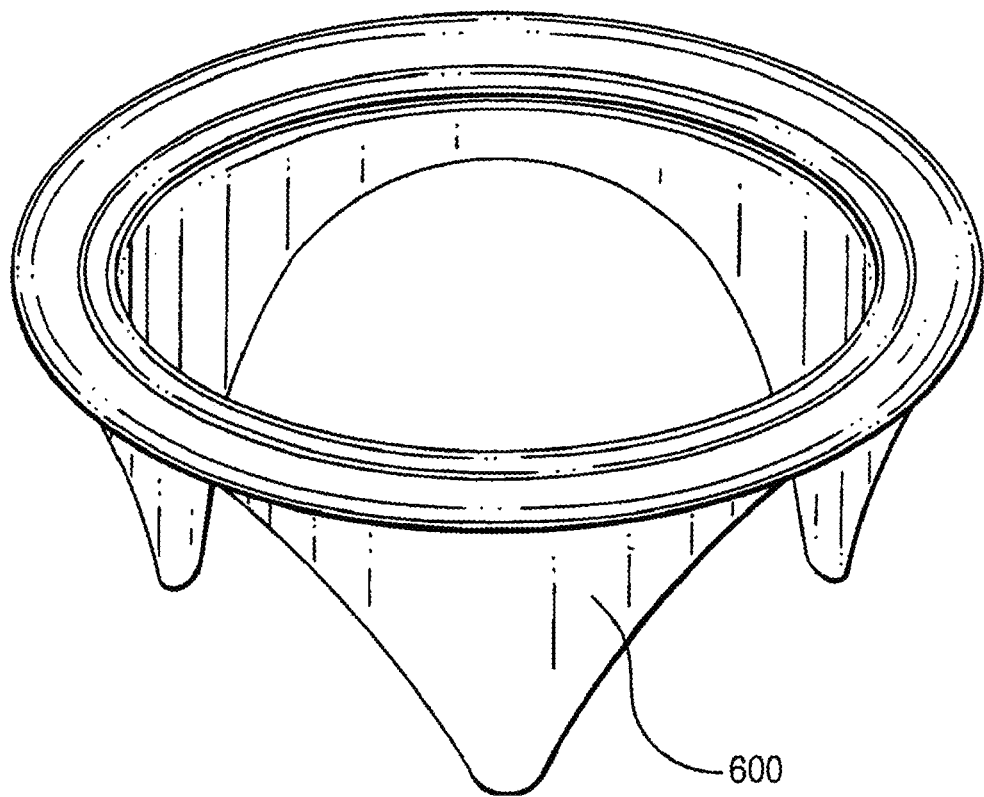

FIGS. 6 and 7 illustrate still further possible components and steps in the manufacture of the illustrative embodiment being described. In particular, these figures illustrate the addition of porcine pericardium tissue 600 over assembly 500, both inside and out, to produce assembly 700. One of the purposes of this is to enhance the durability of the finished valve. Another purpose is to reduce the thrombogenicity of the finished valve. Sutures may be used to secure tissue 600 to assembly 500. Apart from somewhat thickening assembly 700 as compared to assembly 500, the addition of tissue 600 does not significantly change the shape of any portion of the structure.

Although porcine pericardium is mentioned above for component 600, other types of tissue may be used instead if desired. Examples of such other possible tissue for component 600 include any mammalian pericardium (e.g., equine or bovine pericardium).

Figure 8:
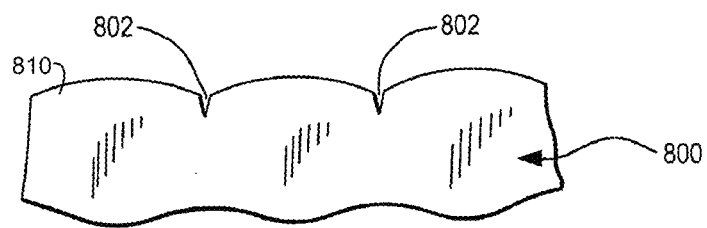
FIG. 8 is a plan view of a tissue sheet prior to assembly to the other components.

FIG. 8 illustrates a further possible component and steps in the manufacture of the illustrative embodiment being described. As shown in FIG. 8, component 800 is a sheet of bovine pericardium that has been die cut to a shape that can be used to form all three leaflets of a finished valve. Note that the lower edge of sheet 800 (as viewed in FIG. 8) is scalloped to conform to the blood-inflow edge (like 120 in FIG. 1) of the finished valve. The upper portion of sheet 800 (as viewed in FIG. 8) will form the three leaflets 810 of the valve. There are shallow downward cuts 802 between the individual leaflet portions adjacent the upper edge of sheet 800, but sheet 800 remains intact so that this single sheet of tissue can be used to form all three leaflets 810 in the finished valve.

Although bovine pericardium is mentioned above for sheet 800, other types of tissue may be used instead as desired. Examples of such other possible tissue for sheet 800 include any mammalian pericardium (e.g., equine or porcine pericardium).

Figure 9:
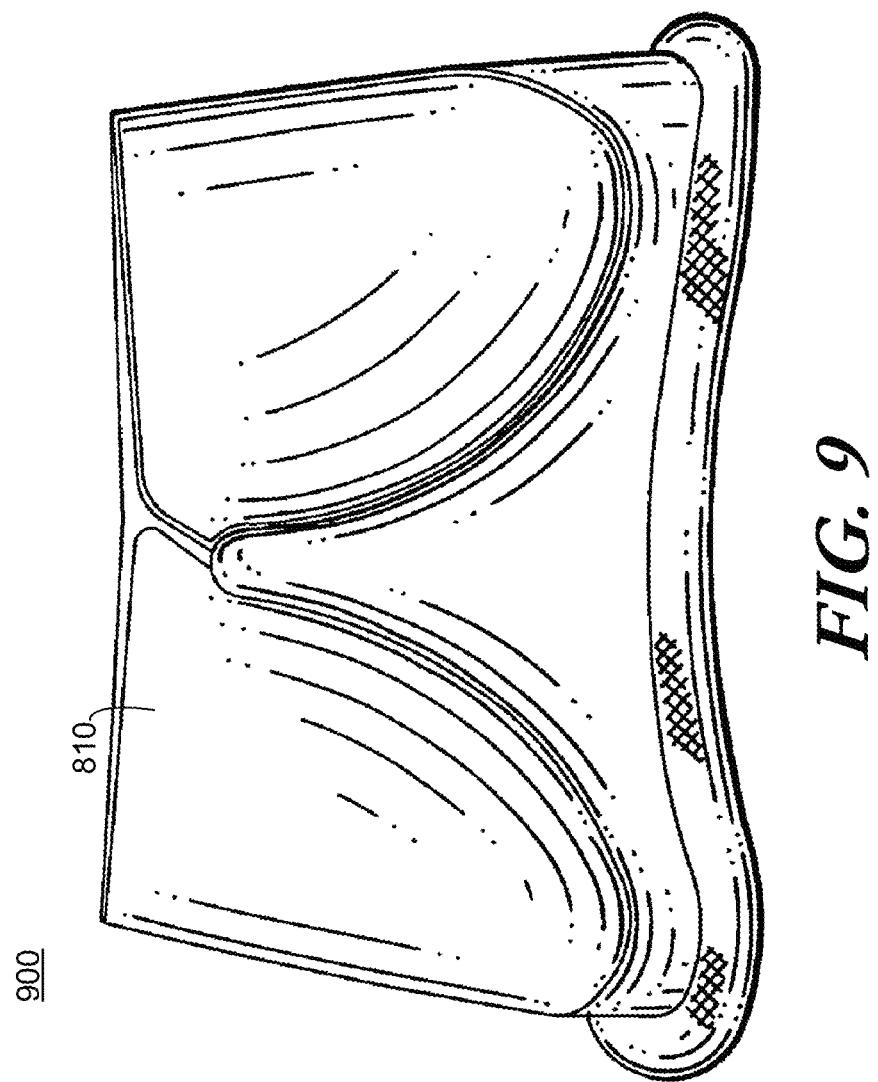
FIG. 9 is a perspective of an illustrative embodiment of a completed prosthetic heart valve.

FIG. 9 illustrates a complete prosthetic heart valve 900 after affixing sheet 800 to assembly 700. In use, valve 900 has the operating characteristics described in the preceding paragraphs. Ideally, the coaptation section of each leaflet may range in size as a particular valve design demands, but generally, will be sufficient to provide some tolerance or ability to form a coaptation junction even if the shape of the valve is distorted during placement.

Figure 10B:
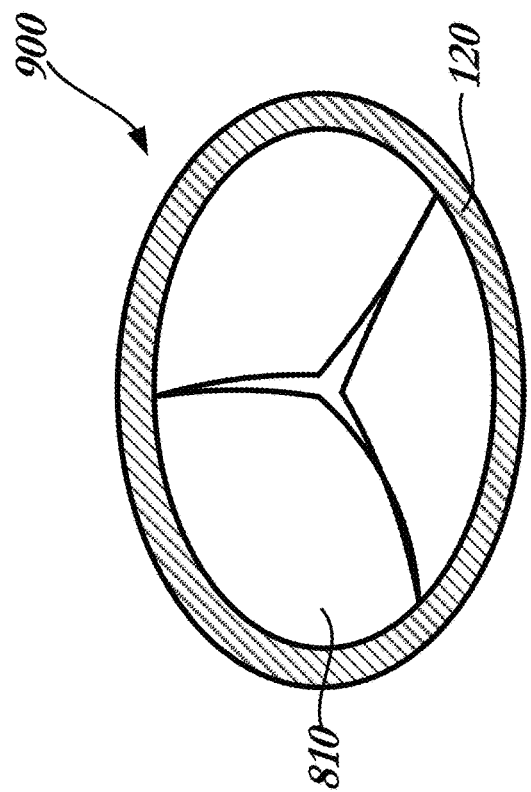
FIG. 10B is a schematic bottom plan view of the prosthetic heart valve of FIG. 5 in an elliptical configuration.
Figure 10A:
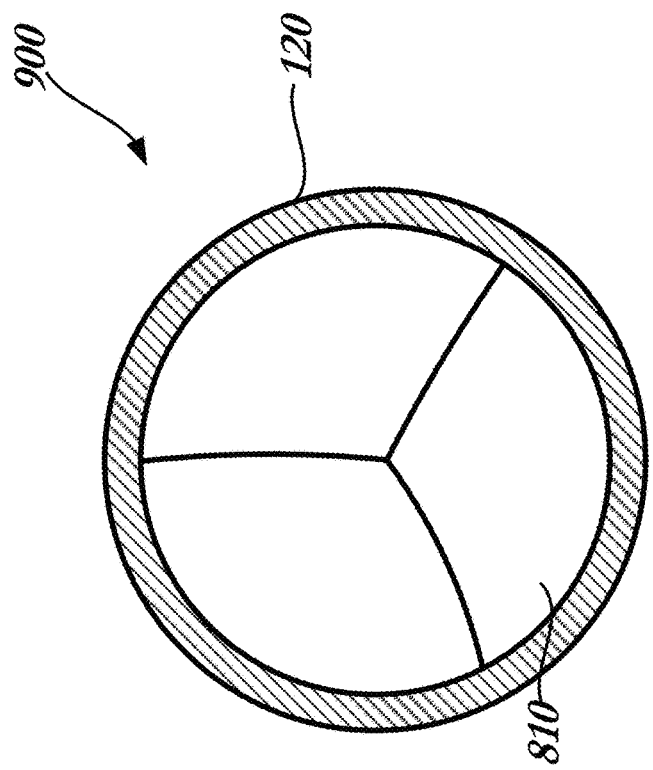
FIG. 10A is a schematic bottom plan view of the prosthetic heart valve of FIG. 5 in a circular configuration.

FIG. 10A illustrates a bottom plan view of the complete prosthetic heart valve 900 shown in FIG. 9. The inflow edge 120 of frame 100 has a generally circular cross-section with a substantially constant diameter along its length. When placed in the annulus of a native heart valve, such as, for example, the tricuspid aortic valve, a substantially fluid-tight fit should result. As seen in FIG. 10A, under ideal conditions, all three leaflets 810 meet to form effective coaptation junctions.

In some applications, the native valve annulus may not be circular, and, in fact, may vary from patient to patient, as may the shape of the aortic sinus or aorta, the angle of the junction between the valve annulus and the aortic sinus, and other local anatomical features. Prosthetic valve 900 should accommodate these anatomical variations in order to function properly. This may result in a distortion in the shape of frame 100 and/or the repositioning of leaflets 810 relative to one another, which can affect the coaptation junctions.

As seen in FIG. 10B, as the frame of the prosthetic heart valve distorts, during beating of the heart, or because of irregularities in the patient's anatomy or the condition of the native valve, such distortion may be translated to the valve assembly, such that not all of the valve leaflets 810 meet to form effective coaptation junctions. This can result in leakage or regurgitation and other inefficiencies which can reduce cardiac performance. Moreover, if the prosthetic valve is not placed optimally and the valve leaflets are not coapting as intended, other long term effects, such as uneven wear of the individual leaflets, can be postulated. As will be appreciated, the distortion of the frame 100 affects the relative positions of the commissure portions, as well as the positions of leaflets 810 relative to one another. The ability of the valve leaflets 810 to fully coapt despite these conditions enables prosthetic valve 900 to function in the manner intended.

One approach for solving the problem of imperfect annulus geometry is to modify or design valve leaflets that coapt despite the non-circular configurations. Instead of this approach, or in addition to this approach, features may be added to a prosthetic heart valve to maintain a substantially circular configuration in a non-circular annulus.

Stiffening components may be added to a prosthetic heart valve to limit the distortion of frame 100. Such stiffening components may be coupled to the frame to reduce the effects of imperfect geometry on valve function and/or performance. Ideally, the stiffening component is coupled to the frame without affecting the hydrodynamic parameters, fatigue, durability or flexibility of the frame.

Features of this aspect of the present invention will be described in connection with the heart valve shown in FIGS. 11-15. It will also be noted that while the inventions herein described are predominately discussed in terms of a tricuspid valve and a frame having a shape as illustrated in FIG. 9, the valve could be any other type of valve, including a bicuspid valve, such as a mitral valve.

Figure 11:
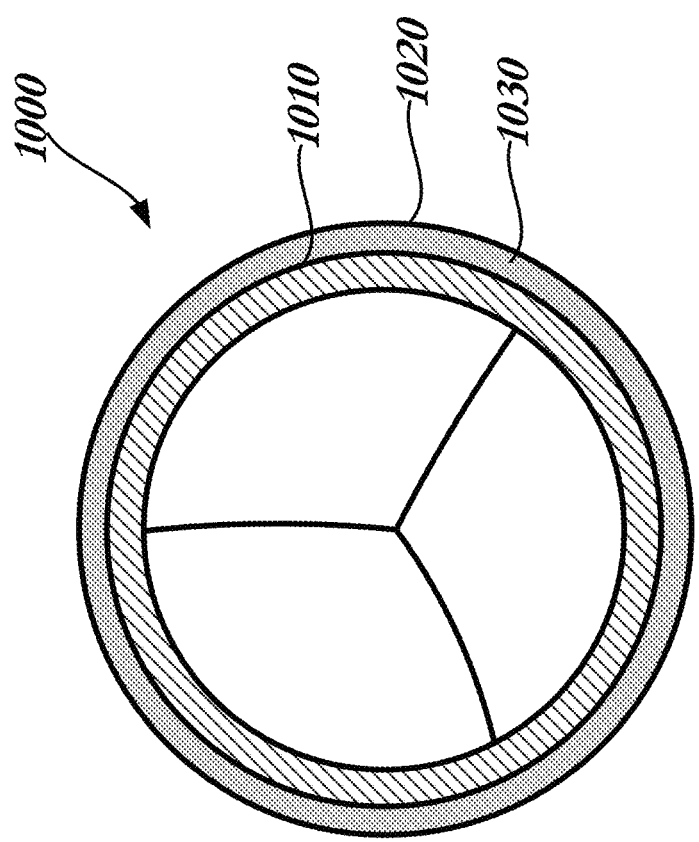
FIG. 11 is a schematic bottom plan view of a prosthetic heart valve having a stiffener.

FIG. 11 illustrates a top view of a prosthetic heart valve 1000 having a frame 1010 coupled to a stiffener 1020. FIG. 11 illustrates stiffener 1020 attached to an outer circumference of frame 1010. Stiffener 1020 may instead be disposed adjacent the inner circumference of frame 1010. Additionally, stiffener 1020 may be fold over the inflow edge so as to be partially disposed about the outer diameter and partially on the inner diameter. In at least some examples, stiffener 1020 is formed as a ring that runs coaxially with the silicone cuff filler ring 400 described in FIG. 4.

Stiffener 1020 may be formed of a metal, polymer or any other suitable biocompatible or biologically inert material. In at least some examples, stiffener 1020 may be formed of a Co—Cr—Ni alloy, such as ELGILOY®. Ideally, the material chosen for the stiffener 1020 is non-corroding when implanted within the human body. Corrosion properties of the stiffener 1020 may be observed in long-term simulated use trials. Stiffener 1020 may be encased in a fabric 1030, which may be the same as or similar to the polyester fabric tube 300 discussed above with reference to FIGS. 2 and 3.

Figure 12B:
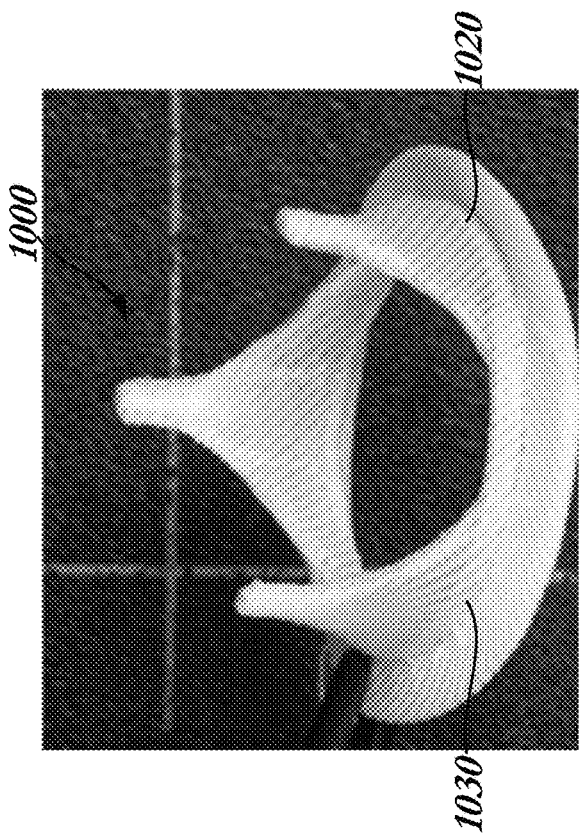
FIGS. 12A and 12B are perspective views of a prosthetic heart valve without leaflets and without a stiffener and with a stiffener, respectively.
Figure 12A:
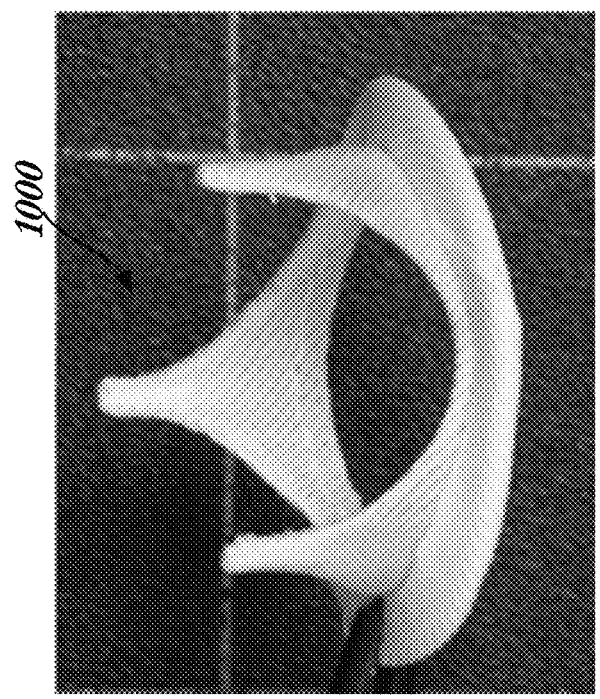

FIG. 12A illustrates a covered frame 1010 for a prosthetic heart valve 1000 and FIG. 12B illustrates a covered frame 1010 for a prosthetic heart valve having a stiffener 1020 encased in fabric 1030 so as to operatively couple the stiffener to the frame. As seen by comparing the two frames, the addition of a stiffener 1020 does not greatly increase the profile of the prosthetic heart valve frame, but provides rigidity and limits ovalization.

Figure 13B:
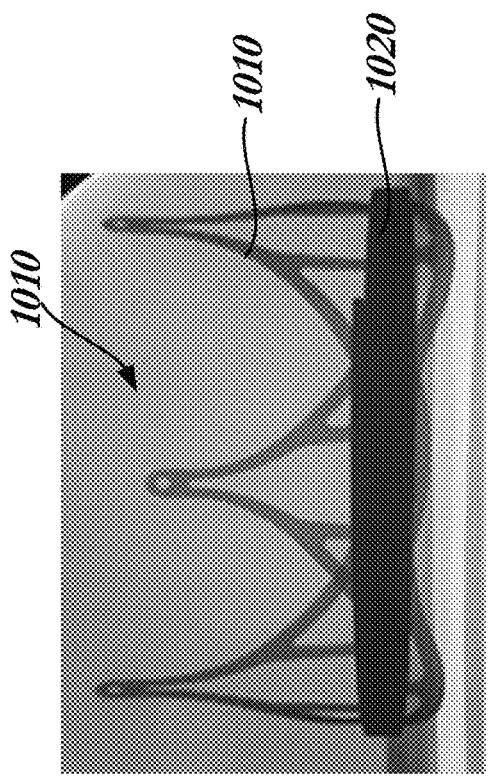
FIGS. 13A and 13B are radiographic images of the valves of FIGS. 12A and 12B, respectively.
Figure 13A:
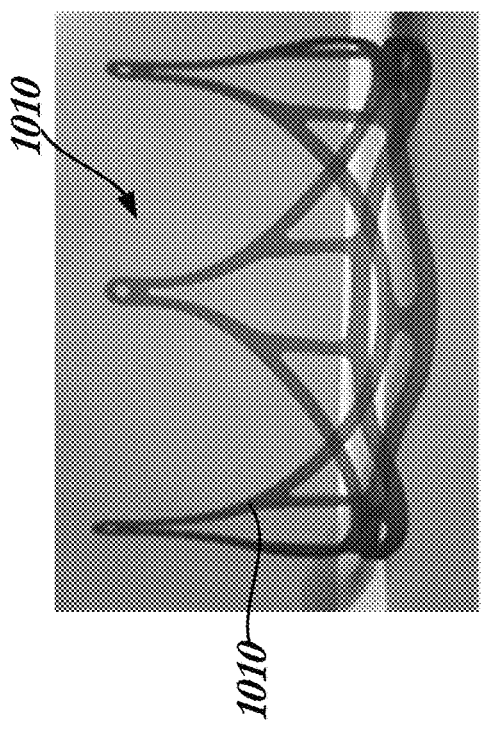

To determine the location of prosthetic heart valve during a surgical procedure, an imaging technique is generally employed. To help locate the prosthetic heart valve 1000 within the patient's body, all or portions of the stiffener 1020 may be formed of a radiopaque material. FIGS. 13A and 13B illustrate radiopaque images of a prosthetic heart valve 1000 with and without a radiopaque stiffener 1020.

Figure 14:
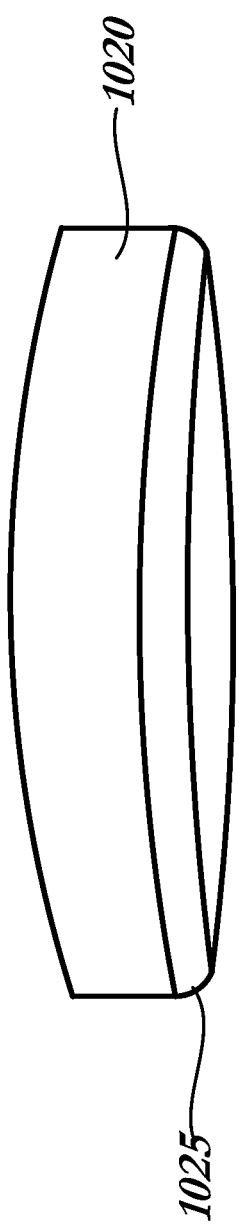
FIG. 14 is a perspective view of a stiffener having a chamfer.
Figure 15:
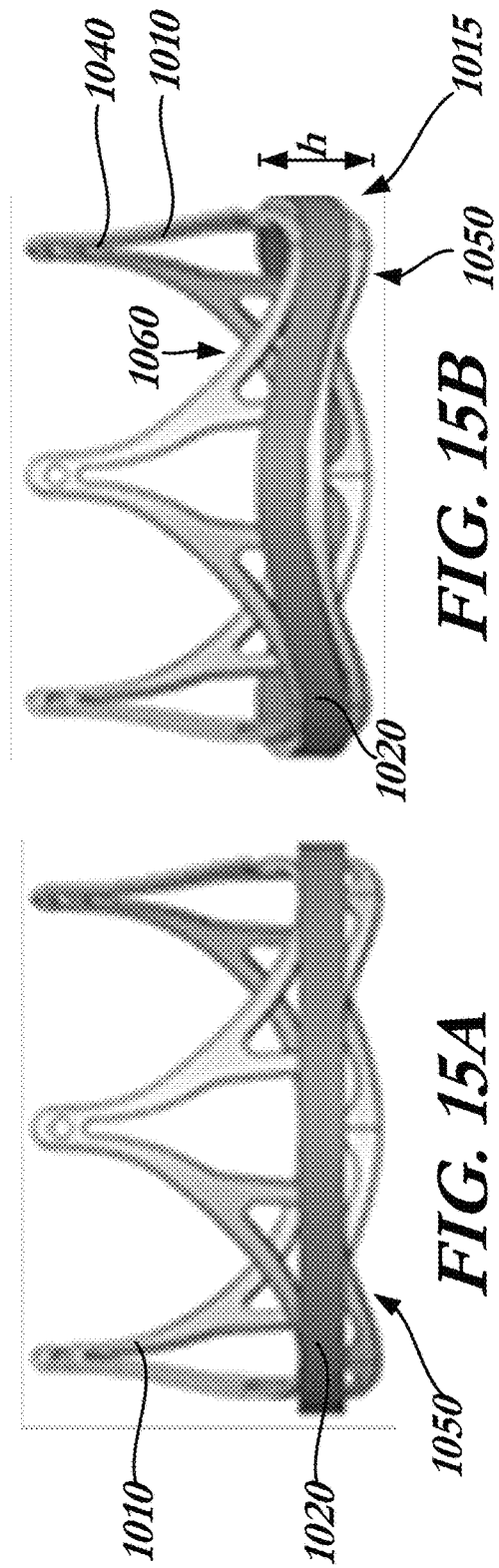
FIGS. 15A and 15B are side views of a prosthetic heart valve frame having a cylindrical stiffener and a scalloped stiffener, respectively.

To further reduce the profile of prosthetic heart valve 1000 and allow suturing as close to the frame 1010 as possible, the edge of the stiffener 1020 may be rounded or a chamfer may be formed in the stiffener 1020, as shown in FIG. 14. While FIG. 14 illustrates that the bottom edge of stiffener 1020 includes a chamfer 1025, it will be understood that top edge of stiffener 1020 may likewise include a chamfer 1025, and that stiffener 1020 may include chamfers 1025 on only one edge or both edges.

FIG. 15A illustrates a cylindrical stiffener 1020 disposed about frame 1010 with a scalloped shape near inflow edge 1050. Stiffener 1020 may also be formed to track the scalloped shape of the inflow edge 1050 of frame 1010, as seen in FIG. 15B, without causing a change in the shape of the frame. Additionally, the height of stiffening ring 1020 may be varied. For example, the minimum distance between the outflow edge 1060 and inflow edge 1050 may be defined as "h" and may be disposed between commissures 1040. Frame 1010 may also include an annulus portion 1015. Stiffener 1020 may be shaped and sized to pass over the midline of the frame annulus portion and have a height less than the minimum distance "h" between the inflow and outflow edges.

Instead of a separate stiffener 1020, the frame 1010 may be made more rigid by outwardly flaring the inflow edge 1050 of the frame 1010. The flared portion of the inflow edge would serve the same purpose of providing resistance against ovalization when the prosthetic heart valve 1000 is placed in imperfect geometry.

Figure 16:
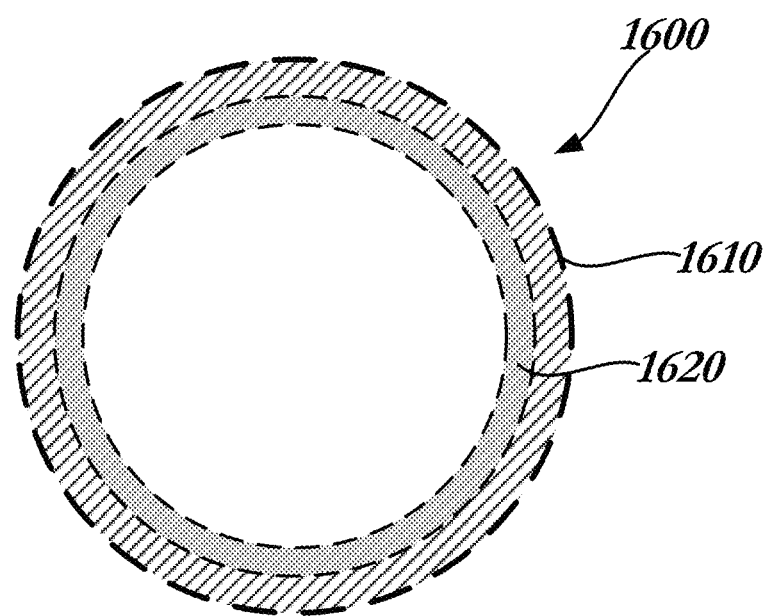
FIG. 16 is a cross-sectional view of a prosthetic heart valve having a frame and a stiffener disposed on the frame's inner diameter.

FIG. 16 is a cross-sectional view of a prosthetic heart valve 1600 having an annular frame 1610 and a stiffener 1620 disposed on the inner diameter of the frame 1610.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A prosthetic heart valve, comprising:
a metallic annular frame having a continuous circumference, and annularly spaced commissure portions and an annulus portion disposed near an inflow edge, the annular frame being scalloped at the inflow edge so as to oscillate between peaks adjacent each of the commissure portions and valleys between adjacent pairs of the commissure portions;
a fabric covering a portion of the frame;
a valve assembly connected to the frame at the commissure portions, the valve assembly including a plurality of leaflets; and
a substantially circular stiffening member closely arranged adjacent an annulus portion of the frame, the stiffening member overlapping with the annular frame and having a top edge, a bottom edge and a continuous surface between the top edge and the bottom edge at all locations around a perimeter of the stiffening member, the stiffening member being scalloped to match oscillation of the annular frame, the bottom edge of the stiffening member extending along the inflow edge of the annular frame around the entire circumference of the annular frame and a substantially constant height from the bottom edge to the top edge, the stiffening member being configured and arranged to limit ovalization of the frame when a radial force is applied to the frame.

2. The prosthetic heart valve of claim 1, wherein the stiffening member includes a ring disposed about a portion of the frame.

3. The prosthetic heart valve of claim 2, wherein the ring includes at least one chamfer.

4. The prosthetic heart valve of claim 1, wherein the stiffening member comprises a metal.

5. The prosthetic heart valve of claim 1, wherein the stiffening member is disposed about the annulus portion of the frame.

6. The prosthetic heart valve of claim 1, wherein the stiffening member is biocompatible.

7. The prosthetic heart valve of claim 1, wherein the stiffening member is disposed about the outer diameter of the frame.

8. The prosthetic heart valve of claim 1, wherein the stiffening member is disposed within the inner diameter of the frame.

9. The prosthetic heart valve of claim 1, wherein the stiffening member is at least partially wrapped in a fabric.

10. The prosthetic heart valve of claim 1, wherein the stiffening member includes at least one chamfer.

11. The prosthetic heart valve of claim 1, wherein a chamfer is formed on the bottom edge the stiffening member.

12. The prosthetic heart valve of claim 1, wherein the stiffening member is operatively coupled to the frame.

13. The prosthetic heart valve of claim 1, wherein the stiffening member is impermeable between the top edge and the bottom edge.

14. The prosthetic heart valve of claim 13, wherein the stiffening member is impermeable to a fluid.

15. The prosthetic heart valve of claim 1, wherein the stiffening member does not include any openings between the top edge and the bottom edge.

16. The prosthetic heart valve of claim 1, wherein the annular frame includes an outflow edge, and at each position around a circumference of the annular frame, a first longitudinal distance between the bottom edge of the stiffening member and the outflow edge of the annular frame is less than a second longitudinal distance between the inflow edge and the outflow edge of the annular frame.

17. The prosthetic heart valve of claim 1, wherein the annular frame includes an outflow edge, and the stiffening member is disposed between the inflow edge and the outflow edge of the annular frame.

18. The prosthetic heart valve of claim 1, wherein the metallic annular frame comprises titanium.

19. The prosthetic heart valve of claim 1, wherein the annular frame includes an outflow edge, and the stiffening member is fully disposed between the inflow edge and the outflow edge of the annular frame.

20. A prosthetic heart valve for use in a native valve annulus, comprising:
    a metallic annular frame having a continuous circumference, and annularly spaced commissure portions and an annulus portion disposed near an inflow edge, the annular frame being scalloped at the inflow edge so as to oscillate between peaks adjacent each of the commissure portions and valleys between adjacent pairs of the commissure portions;
    a fabric covering a portion of the frame;
    a valve assembly connected to the frame at the commissure portions, the valve assembly including a plurality of leaflets; and
    a stiffening member disposed within an annulus portion of the frame and overlapping with the frame, and having a top edge, a bottom edge, a substantially constant height from the bottom edge to the top edge, and a continuous surface between the top edge and the bottom edge at all locations around a perimeter of the stiffening member, the stiffening member being scalloped to match oscillation of the annular frame, the bottom edge of the stiffening member extending along the inflow edge of the annular frame around the entire circumference of the annular frame, the stiffening member being configured and arranged to define and maintain a substantially circular orifice for blood flow through the annular frame when a radial force is applied to the frame from the native valve annulus.

21. The prosthetic heart valve of claim 20, wherein the prosthetic heart valve is configured and arranged for deployment in the aortic native valve annulus.

* * * * *